(12) United States Patent
Takei et al.

(10) Patent No.: US 8,918,286 B2
(45) Date of Patent: Dec. 23, 2014

(54) ENVIRONMENTAL MEASUREMENT SYSTEM AND ENVIRONMENTAL MEASUREMENT METHOD

(75) Inventors: Fumio Takei, Kawasaki (JP); Kazushi Uno, Kawasaki (JP); Takeo Kasajima, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 306 days.

(21) Appl. No.: 13/572,956

(22) Filed: Aug. 13, 2012

(65) Prior Publication Data

US 2012/0310535 A1 Dec. 6, 2012

Related U.S. Application Data

(63) Continuation of application No. PCT/JP2010/053963, filed on Mar. 10, 2010.

(51) Int. Cl.
 *G01N 25/68* (2006.01)
 *G01N 25/62* (2006.01)
 *G01N 21/65* (2006.01)
 *G01N 21/81* (2006.01)
 *G01N 21/77* (2006.01)

(52) U.S. Cl.
 CPC ........ *G01N 25/62* (2013.01); *G01N 2021/7773* (2013.01); *G01N 21/65* (2013.01); *G01N 21/7703* (2013.01); *G01N 21/81* (2013.01)
 USPC .......................................................... 702/3

(58) Field of Classification Search
 CPC .................................................... G01N 25/68
 USPC .......................................................... 702/3
 See application file for complete search history.

(56) References Cited

U.S. PATENT DOCUMENTS 6,022,138 A * 2/2000 Sonander ........................ 374/28
6,926,439 B2 * 8/2005 Zlochin ........................... 374/20

FOREIGN PATENT DOCUMENTS

| JP | H2-171628 | 7/1990 |
|---|---|---|
| JP | H5-60689 | 3/1993 |
| JP | H6-43041 | 2/1994 |
| JP | H9-113472 | 5/1997 |
| JP | H10-104363 | 4/1998 |
| JP | 2002-267242 A1 | 9/2002 |
| JP | 2003-130863 A1 | 5/2003 |
| JP | 2003-270141 A1 | 9/2003 |
| JP | 2005-351663 A1 | 12/2005 |

OTHER PUBLICATIONS

International Search Report for International Application No. PCT/JP2010/053963 dated May 25, 2010.

* cited by examiner

*Primary Examiner* — Stephen Cherry
(74) *Attorney, Agent, or Firm* — Kratz, Quintos & Hanson, LLP

(57) ABSTRACT

An optical fiber is provided with a first measurement portion and a second measurement portion. The first measurement portion is provided with a heater and a hygroscopic layer made of a resin in which a material having a deliquescent property is dispersed. Meanwhile, the second measurement portion is provided with the heater and a non-hygroscopic layer having a lower moisture absorption capacity than the capacity of the hygroscopic layer. The heater is brought into heat generation by being supplied with electric power, and temperatures at the second measurement portion and temperatures at the first measurement portion are measured with a temperature measurement device. Then, an analyzer calculates a humidity based on an integrated value of differences between the temperatures at the first measurement portion and the temperatures at the second measurement portion.

13 Claims, 9 Drawing Sheets

ENVIRONMENTAL MEASUREMENT SYSTEM AND ENVIRONMENTAL MEASUREMENT METHOD

CROSS-REFERENCE TO RELATED APPLICATION

This application is a continuation of International Application No. PCT/JP2010/053963 filed Mar. 10, 2010 and designated the U.S., the entire contents of which are incorporated herein by reference.

FIELD

The embodiments discussed herein are related to an environmental measurement system and an environmental measurement method of measuring temperatures and humidities.

BACKGROUND

Prevention of global warming has been an urgent issue in recent years, and all the aspects of society are requested to achieve power saving due to this reason. For example, an enormous amount of electric power is consumed for air conditioning in a factory, a large office building, an Internet data center or the like (hereinafter referred to as a "facility such as an office building") and there are demands for both of power saving in such air-conditioning equipment and optimization of air conditioning.

In order to optimize air conditioning in a facility such as an office building, it is preferable to measure temperatures and humidities in many positions of the facility and to control air-conditioning equipment based on measurement results. When there are few measurement positions, a temperature sensor and a humidity sensor may individually be installed in the respective positions. The temperature sensor usable for this purpose may be a thermocouple, a platinum resistance temperature detector, a thermistor, an expansion thermometer, and the like. Meanwhile, the humidity sensor usable may be an electric resistance detection type humidity sensor, an electric capacitance detection type humidity sensor, and the like.

However, when the aforementioned sensors are used in many measurement positions, a large number of sensors are used, which leads to an increase in cost of the entire system. In the meantime, an increase in the number of sensors leads to an increase in cost for maintenance. In this regard, there is a proposal to measure a temperature in a facility such as an office building by use of a temperature measurement device employing an optical fiber as a temperature sensor (such a device will be hereinafter referred to as an "optical fiber temperature measurement device").

The optical fiber temperature measurement device is configured to measure a temperature by inputting a laser beam into an optical fiber and detecting Raman scattered light generated inside the optical fiber. The device may measure temperature distribution in a longitudinal direction of the optical fiber within a short time.

Meanwhile, there is also a proposal to measure a humidity based on the principle of a typical wet-and-dry-bulb hygrometer by using an optical fiber temperature measurement device. A humidity measurement device of this type is configured to maintain a portion of an optical fiber in a moist state by continuously supplying water thereto and to calculate a relative humidity in an atmosphere by use of a difference between a temperature at a moist portion maintained in the moist state and a temperature at a dry portion.

Patent Document 1: Japanese Laid-open Patent Publication No. 02-171628
Patent Document 2: Japanese Laid-open Patent Publication No. 10-104363

The above-described humidity measurement device using the optical fiber is provided with a water tank and is configured to supply water from the water tank to the moist portion by means of a capillary action. However, in order to measure the humidity over a long time, it is preferably to perform an operation of checking whether the water is left in the water tank and refilling the water tank if the water is not left. When there are few measurement positions, it may be possible to check the water and to refill the water tank manually. However, when there are many measurement positions, it is difficult to check the water and to refill the water tank manually and equipment for automating the operation is used. Such automation may lead to an increase in size of a system and may result in an increase in cost of the entire system and an increase in cost for maintenance of the system.

SUMMARY

According to an aspect, an environmental measurement system includes an optical fiber including a first measurement portion covered with a hygroscopic layer having a moisture absorption capacity to absorb moisture in an atmosphere, and a second measurement portion covered with a non-hygroscopic layer having a lower moisture absorption capacity than the capacity of the hygroscopic layer; a heater configured to heat the first measurement portion and the second measurement portion; a temperature measurement device configured to input light into the optical fiber, and to receive backscattered light outputted from the optical fiber to measure temperature distribution in a longitudinal direction of the optical fiber; an analyzer configured to analyze a variation over time of the temperature distribution outputted from the temperature measurement device to calculate a temperature and a humidity in a measurement position where the first measurement portion and the second measurement portion are installed; and a control device configured to control the heater, the temperature measurement device, and the analyzer.

The object and advantages of the invention will be realized and attained by means of the elements and combinations particularly pointed out in the claims.

It is to be understood that both the foregoing general description and the following detailed description are exemplary and explanatory and are not restrictive of the invention.

DESCRIPTION OF EMBODIMENTS

Embodiments will be described below with reference to the accompanying drawings.

First Embodiment

Figure 1:
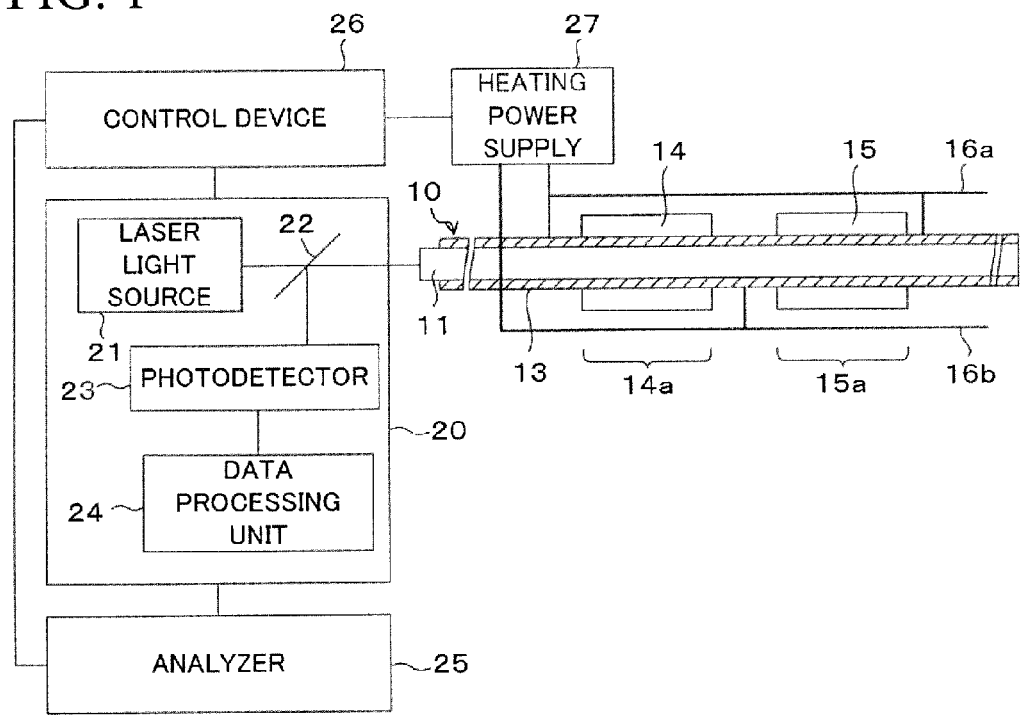
FIG. 1 is a block diagram illustrating an outline of an environment measurement system according to a first embodiment.
Figure 2A:
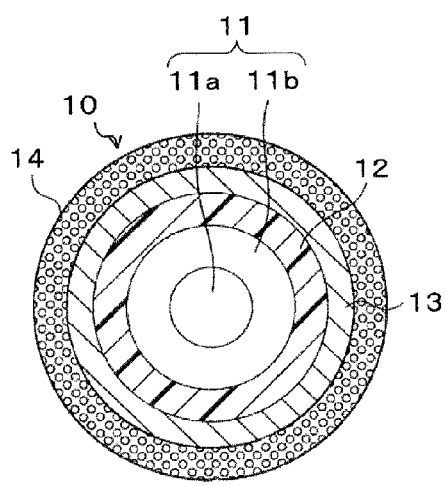
FIGS. 2A and 2B are cross-sectional views of portions of an optical fiber.
Figure 2B:
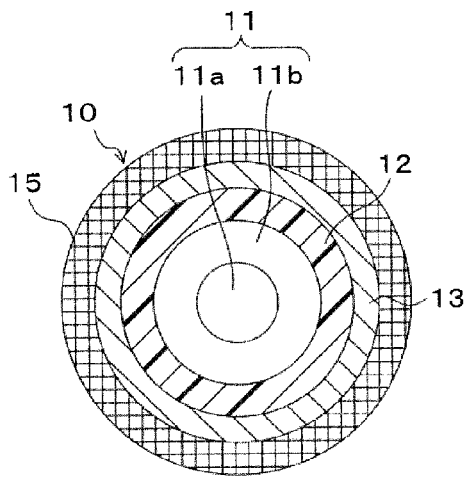

FIG. 1 is a block diagram illustrating an outline of an environment measurement system according to a first embodiment, and FIGS. 2A and 2B are cross-sectional views of portions of an optical fiber.

As illustrated in FIG. 1, an environmental measurement system of this embodiment includes an optical fiber 10, an optical fiber temperature measurement device 20, an analyzer 25, a control device 26, and a heating power supply 27.

The optical fiber 10 includes a core wire 11 configured to propagate a laser beam, an insulating covering layer 12 (illustration of which is omitted in FIG. 1) configured to cover the core wire 11, a heat generation layer (a heater) 13 provided on the insulating covering layer 12, and a hygroscopic layer 14 and a non-hygroscopic layer 15 provided on the heat generation layer 13. A portion provided with the hygroscopic layer 14 will be hereinafter referred to as a wet measurement portion (a first measurement portion) 14a and a portion provided with the non-hygroscopic layer 15 will be hereinafter referred to as a dry measurement portion (a second measurement portion) 15a.

As depicted in FIGS. 2A and 2B, the core wire 11 includes a core 11a and a clad 11b arranged around the core 11a. Light is enclosed in and transmitted on the core 11a by means of a difference in the refractive index between the core 11a and the clad 11b.

The insulating covering layer 12 is made of an insulating material such as polyurethane having a certain amount of heat resistance. The heat generation layer 13 may be made of a material which performs resistance heating when electricity is supplied thereto. The heat generation layer 13 is made of a conductive material containing silver or carbon, for example.

The non-hygroscopic layer 15 is made of an insulating material having a non-hygroscopic property or a water-repellent property such as polyvinylidene fluoride, polyvinylidene chloride or organosilicone resin. Meanwhile, the hygroscopic layer 14 is made of a material prepared by dispersing particulates of a material having a deliquescent property such as magnesium chloride, calcium chloride, sodium acetate or diphosphorus pentoxide into insulating resin to be used as a parent material. It is preferable that the non-hygroscopic layer 15 be lacking in an ability (a moisture absorption ability) to absorb moisture in an atmosphere or having such a moisture absorption ability lower than that of the hygroscopic layer 14.

It is preferable that the hygroscopic layer 14 and the non-hygroscopic layer 15 have either the same specific heat or substantially the same specific heat in order to facilitate data processing. For this reason, the parent material of the hygroscopic layer preferably uses the same resin as the one used in the non-hygroscopic layer 15. Here, the hygroscopic layer 14 may be made of resin having a deliquescent property or a strong hygroscopic property in itself. Such resin may be polystyrene sulfonate, quaternized polyvinylpyridine, and the like. As schematically illustrated in FIG. 1, the hygroscopic layer 14 and the non-hygroscopic layer 15 are arranged at a given interval along the longitudinal direction of the optical fiber 10.

As described later, in this embodiment, the wet measurement portion 14a and the dry measurement portion 15a are installed in the same measurement position to measure a temperature and a humidity in the measurement position. When there is just one measurement position, a single set of the hygroscopic layer 14 and the non-hygroscopic layer 15 may be provided in the position. When there are two or more measurement positions, a plurality of sets of the hygroscopic layer 14 and the non-hygroscopic layer 15 may be provided along the longitudinal direction of the optical fiber 10.

The temperature measurement device 20 includes a laser light source 21, a beam splitter 22, a photodetector 23, and a data processing unit 24. The core wire 11 of the optical fiber 10 is optically connected to the laser light source 21 and the beam splitter 22.

A laser beam (a laser pulse) is emitted from the laser light source 21 at a given time interval. The laser beam emitted from the laser light source 21 passes through the beam splitter 22 and enters the core wire 11 of the optical fiber 10, and then propagates inside the optical fiber 10 in the longitudinal direction thereof. A portion of the light propagating inside the optical fiber 10 is backscattered by molecules which constitute the optical fiber 10 (the core wire 11). The backscattered light goes back in the optical fiber 10 and is emitted from an end on the light source side. Then, the backscattered light is reflected by the beam splitter 22 and is inputted to the photodetector 23.

Figure 3:
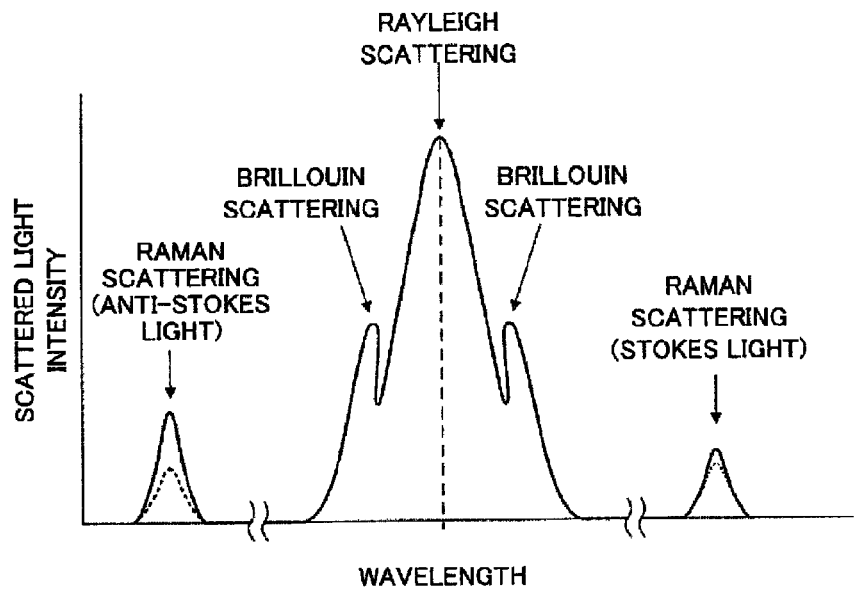
FIG. 3 is a view illustrating a spectrum of backscattered light.

As illustrated in FIG. 3, the backscattered light generated inside the optical fiber 10 includes Rayleigh scattered light, Brillouin scattered light, and Raman scattered light. The Rayleigh scattered light is the light having the same wavelength as the incident light. Meanwhile, each of the Brillouin scattered light and the Raman scattered light is the light having a wavelength shifted from the wavelength of the incident light.

The Raman scattered light includes Stokes light shifted to a longer wavelength than the incident light and anti-Stokes light shifted to a shorter wavelength than the incident light. Although a shift amount of the each of the Stokes light and the anti-Stokes light depends on the wavelength of the laser beam, the materials constituting the optical fiber 10 (the core wire 11), and the like, the shift amount is usually around 50 nm. In the meantime, an intensity of each of the Stokes light and the anti-Stokes light varies with the temperature. Here, the Stokes light has a smaller amount of variation with the temperature, whereas the anti-Stokes light has a larger amount of variation with the temperature. In other words, the Stokes light has smaller temperature dependence and the anti-Stokes light has larger temperature dependence. The photodetector 23 separates the Stokes light and the anti- Stokes light from the backscattered light and detects an amount of each of the separated light factors.

Figure 4:
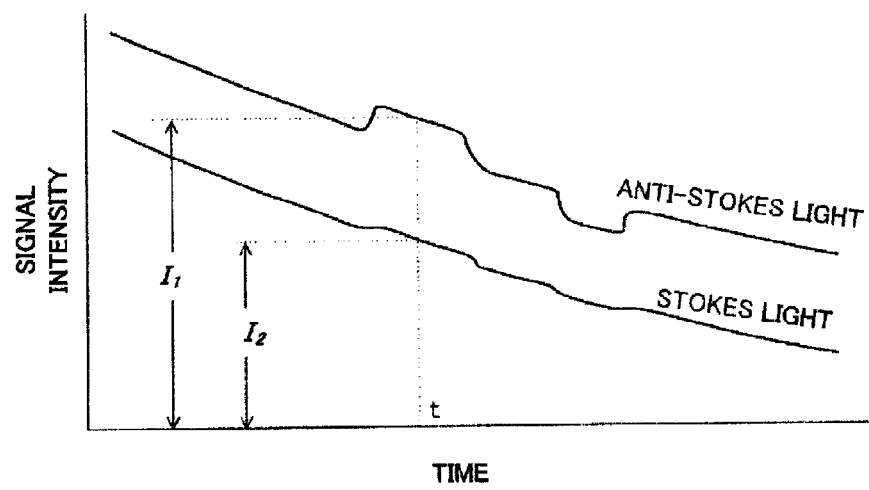
FIG. 4 is a view illustrating an example of variations over time of Raman scattered light intensities.

FIG. 4 is a view illustrating an example of variations over time of Raman scattered light intensities, in which the horizontal axis indicates time and the vertical axis indicates signal intensities detected by the photodetector 23. The photodetector 23 detects the Stokes light and the anti-Stokes light for a predetermined period from immediately after incidence of the laser pulse on the optical fiber 10. If the temperature is uniform across the entire length of the optical fiber 10, a signal intensity is reduced over time based on a point of incidence of the laser pulse on the optical fiber 10. In this case, the time on the horizontal axis indicates a distance from an end on the light source side of the optical fiber 10 to a position of generation of the backscattered light while the reduction in the signal intensity over time represents attenuation of the light caused by the optical fiber 10.

If the temperature is not uniform across the longitudinal direction of the optical fiber 10, namely, when there are a high-temperature portion and a low-temperature portion along the longitudinal direction, for example, the signal intensities of the Stokes light and the anti-Stokes light do not attenuate uniformly. Instead, peaks and valleys emerge in the curves indicating the variations over time of the signal intensities as illustrated in FIG. 4. In FIG. 4, an intensity of the anti-Stokes light at a given time point t is defined as $I_1$ while an intensity of the Stokes light at the time point t is defined as $I_2$.

Figure 5:
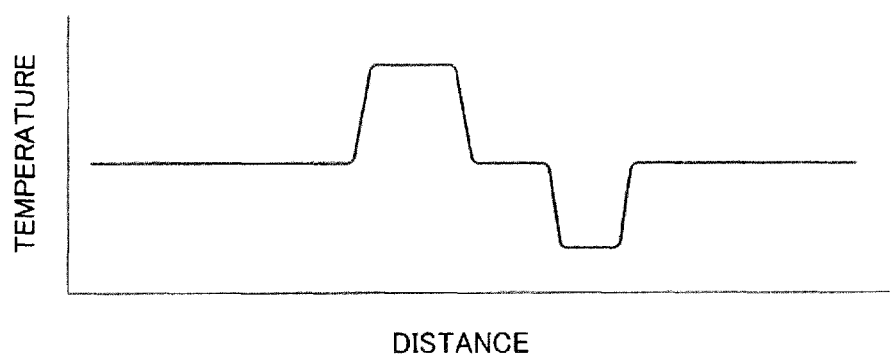
FIG. 5 is a view illustrating a result obtained by calculating a ratio $I_1/I_2$ at various time points based on the variations over time of the Raman scattered light intensities illustrated in FIG. 4, converting the scale of the horizontal axis (time) in FIG. 4 into the distance, and converting the scale of the vertical axis (signal intensity) in FIG. 4 into the temperature.

FIG. 5 is a view illustrating a result obtained by calculating a ratio $I_1/I_2$ at various time points based on the variations over time of the Raman scattered light intensities illustrated in FIG. 4, converting the scale of the horizontal axis (time) in FIG. 4 into the distance, and converting the scale of the vertical axis (signal intensity) in FIG. 4 into the temperature. As illustrated in FIG. 5, temperature distribution in the longitudinal direction of the optical fiber 10 may be measured by calculating the intensity ratio ($I_1/I_2$) of the anti-Stokes light to the Stokes light.

Calculation of the intensity ratio between the anti-Stokes light and the Stokes light is executed by the data processing unit 24. Data on the temperature distribution in the longitudinal direction of the optical fiber 10 are outputted from the data processing unit 24 at given time intervals. The analyzer 25 accumulates the data on the temperature distribution outputted from the temperature measurement device 20, analyzes the variations over time of the temperature distribution, and calculates temperatures and humidities in the position where the wet measurement portion 14a and the dry measurement portion 15a are installed.

The heating power supply 27 supplies electric power to the heat generation layer 13 through electric wires 16a and 16b installed along the optical fiber 10 and thus brings the heat generation layer 13 into resistance heating. Here, two tension members may be provided on both sides of the optical fiber in order to protect the optical fiber. In the case of using the optical fiber configured as described above, the tension members may be used as the wires 16a and 16b. Meanwhile, in FIG. 1, a voltage is applied between two end portions of each of the hygroscopic layer 14 and the non-hygroscopic layer 15 so as to bring the portions corresponding to the hygroscopic layer 14 and the non-hygroscopic layer 15 into heat generation. However, when the optical fiber 10 is short, it may be also possible to bring the entire heat generation layer 13 into heat generation by applying a voltage between two end portions of the optical fiber 10. The control device 26 controls an operational status of the entire system.

In this embodiment, the wet measurement portion 14a and the dry measurement portion 15a are installed in the same measurement position. Then, after the hygroscopic layer 14 of the optical fiber 10 is caused to absorb the moisture in the air (the atmosphere), the electricity is supplied to the heat generation layer 13 by operating the heating electric supply 27. The temperature measurement device 20 detects the temperature distribution in the longitudinal direction of the optical fiber 10 based on the detection results of the Raman scattered light generated inside the optical fiber 10 and outputs the data on the temperature distribution. The analyzer 25 accumulates the data on the temperature distribution outputted from the temperature measurement device 20 and monitors the temperature variations at the wet measurement portion 14a and the dry measurement portion 15a.

Figure 6:
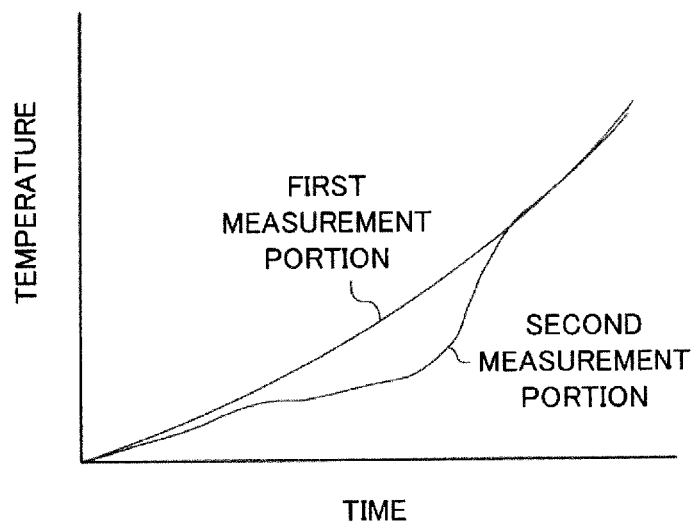
FIG. 6 is a view illustrating an example of temperature variations monitored at a wet measurement portion and a dry measurement portion after starting supply of electric power to a heat generation layer.

FIG. 6 is a view illustrating an example of the temperature variations monitored at the wet measurement portion 14a and the dry measurement portion 15a after starting supply of the electricity to the heat generation layer 13, in which the horizontal axis indicates the time and the vertical axis indicates the temperature. As illustrated in FIG. 6, the temperature at the dry measurement portion 15a rises almost linearly over time. On the other hand, the temperature rise rate is slow at the wet measurement portion 14a for a given period from the start of supply of the electricity but thereafter the temperature rises rapidly. This aspect is attributed to the fact that the moisture absorbed in the hygroscopic layer 14 evaporates and draws heat of evaporation after the start of supply of the electricity and then stops drawing the heat of evaporation when a certain amount of the moisture has evaporated.

In FIG. 6, an area surrounded by a curve indicating the temperature variation at the dry measurement portion 15a and a curve indicating the temperature variation at the wet measurement portion 14a has a relation with the moisture in the atmosphere. Specifically, the area of this portion becomes larger when the humidity in the atmosphere is higher. Accordingly, the humidity in the atmosphere may be calculated by integrating the differences between the temperatures at the dry measurement portions 15a and the temperatures at the wet measurement portion 14a.

Figure 7:
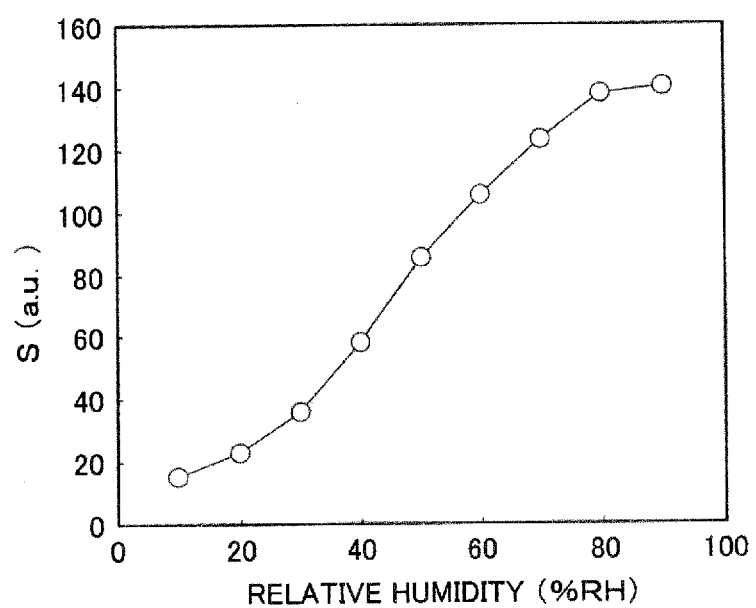
FIG. 7 is a view illustrating a relation between a relative humidity and an area S.

FIG. 7 is a view illustrating a relation between a relative humidity (% RH) and the area S (in an arbitrary unit: a.u.) of the portion surrounded by the curve indicating the temperature variation at the dry measurement portion 15a and the curve indicating the temperature variation at the wet measurement portion 14a. Here, the horizontal axis indicates the relative humidity and the vertical axis indicates the area S.

In this embodiment, the relation between the area S and the relative humidity is obtained in advance and a humidity conversion table indicating the relation between these factors is stored in the analyzer 25. The data on the temperature distribution in the longitudinal direction of the optical fiber 10 are inputted from the temperature measurement device 20 to the analyzer 25, and the analyzer 25 calculates the area S by integrating the differences between the temperatures at the dry measurement portion 15a and the temperatures at the wet measurement portion 14a. Then, the analyzer 25 converts the value of the area S into the humidity in the atmosphere by using the humidity conversion table stored in advance. Here, instead of the humidity conversion table, a relational expression defining the relation between the area S and the humidity may be obtained and the relational expression may be stored in the analyzer 25.

Figure 8:
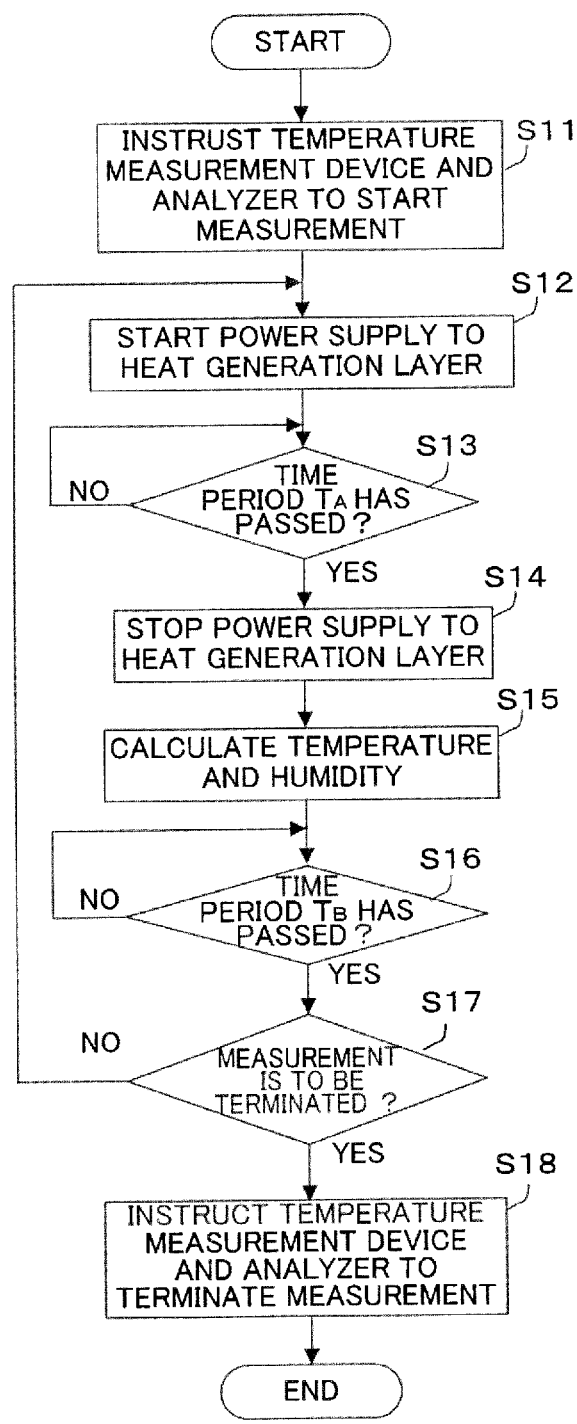
FIG. 8 is a flowchart illustrating an environmental measurement method according to the embodiment.
Figure 9:
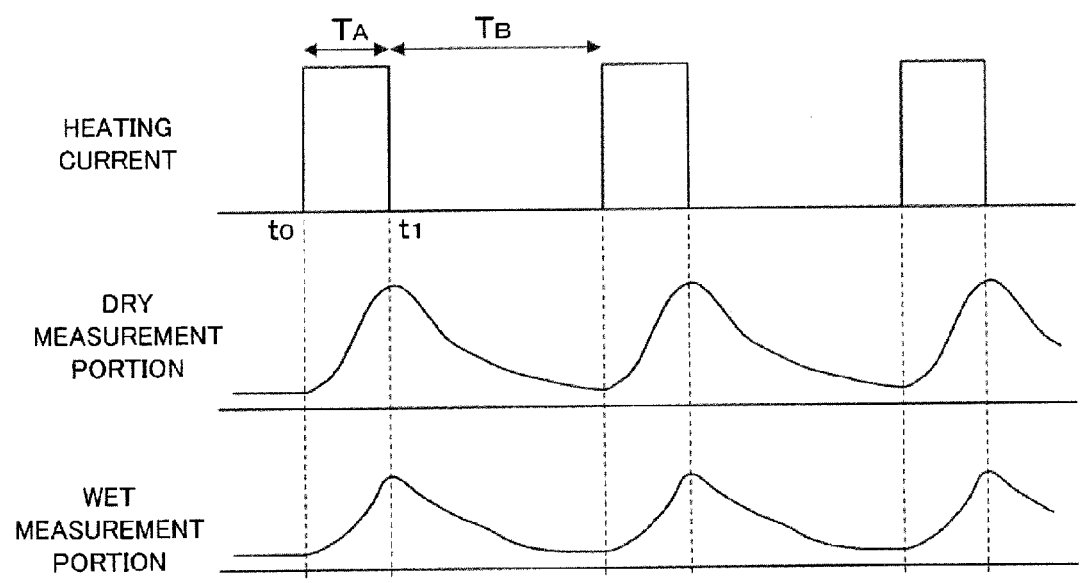
FIG. 9 is a timing chart indicating electric power to be supplied to the heat generation layer and the temperature variations at the wet measurement portion and the dry measurement portion.

FIG. 8 is a flowchart illustrating an environmental measurement method according to this embodiment. Meanwhile, FIG. 9 is a timing chart indicating a heating current to be supplied to the heat generation layer, and the temperature variations at the dry measurement portion 15a and the wet measurement portion 14a. Here, the dry measurement portion 15a and the wet measurement portion 14a are assumed to be installed in the same measurement position.

First, in step S11, the control device 26 outputs a signal for instructing the temperature measurement device 20 and the analyzer 25 to start measurement. Accordingly, the temperature measurement device 20 outputs the laser pulse from the laser light source 21, detects the Raman scattered light with the photodetector 23, and thereby measures the temperature distribution in the longitudinal direction of the optical fiber 10. Since the heating power supply 27 is not operated at this time, the data on the temperature distribution in the longitudinal direction of the optical fiber 10 contain the data on the temperature in the measurement position where the wet measurement portion 14a and the dry measurement portion 15a are installed.

Here, the data on the temperature distribution are outputted from the temperature measurement device 20 at given time intervals during a period from the start of the measurement in step S11 to an end of the measurement in step S18. The data on the temperature distribution outputted from the temperature measurement device 20 are transmitted to the analyzer 25 and are accumulated in the analyzer 25.

Next, in step S12, the control device 26 outputs a signal for instructing the heating power supply 27 to start an operation. Accordingly, the heating power supply 27 applies the given voltage to the heat generation layer 13 at the wet measurement portion 14a and the dry measurement portion 15a and brings the heat generation layer 13 into resistance heating. Meanwhile, the signal for instructing the heating power supply 27 to start the operation is also transmitted to the analyzer 25. Accordingly, the analyzer 25 identifies time $t_0$ when the heating operation is started.

Next, in step S13, the control device 26 judges whether or not a predetermined time period $T_A$ (10 minutes, for example) has passed since the start of power supply to the heat generation layer 13. The predetermined time period $T_A$ is set in accordance with the time for sufficiently evaporating the moisture absorbed in the hygroscopic layer 14. The method transitions from step S13 to step S14 when the control device 26 judges that the predetermined time period $T_A$ has passed.

In step S14, the control device 26 outputs a signal for instructing the heating power supply 27 to stop the operation. Accordingly, the power supply to the heat generation layer 13 is stopped. The signal for instructing the heating power supply 27 to stop the operation is also transmitted to the analyzer 25. Accordingly, the analyzer 25 identifies time $t_1$ when the power supply to the heat generation layer 13 is stopped.

Next, in step S15, the analyzer 25 calculates the temperature and the humidity in the measurement position where the dry measurement portion 15a and the wet measurement portion 14a are installed based on the accumulated data on the temperature distribution. In this embodiment, the temperature in the measurement position is determined by calculating an average value of the temperatures at the dry measurement portion 15a measured before the electric power is supplied to the heat generation layer 13. In the meantime, the humidity in the measurement position is determined by causing the analyzer 25 to integrate the differences between the temperatures at the dry measurement portion 15a and the temperatures at the wet measurement portion 14a and to convert the integrated value into the humidity value by using the humidity conversion table.

In step S16, the control device 26 judges whether or not a predetermined time period $T_B$ (15 to 20 minutes, for example) has passed since the stop of power supply to the heat generation layer 13. The hygroscopic layer 14 absorbs the moisture in the atmosphere and recovers the initial state during the period from the stop of power supply to the heat generation layer 13 to the lapse of the predetermined time period $T_B$. Instead, the control device 26 may sample the temperatures at the dry measurement portion 15a and the wet measurement portion 14a at given time intervals and judge the lapse of the predetermined time period $T_B$ when the control device 26 confirms that there is no temperature drop any longer.

The method transitions from step S16 to step S17 when the predetermined time period $T_B$ has passed. Here, the control device 26 judges whether or not it is appropriate to terminate the measurement. When the answer is no, the method returns to step S12 and starts the power supply to the heat generation layer 13, and then repeats the above-described processing. In this way, the temperatures and the humidities in the measurement position are measured at given time intervals.

When a judgment is made in step S17 that the measurement is to be terminated, the method transitions to step S18 in which the control device 26 outputs a signal indicating termination of the measurement to the temperature measurement device 20 and the analyzer 25. Thus, the measurement is terminated.

In this embodiment, the single optical fiber 10 may measure the temperatures and the humidities in a plurality (100 or more, for example) of measurement positions at the same time. Accordingly, this embodiment involves a simpler system configuration as compared to a system constructed by individually installing a temperature sensor and a humidity sensor in each of measurement positions, thereby reducing costs for constructing the system and costs for maintenance. Moreover, this embodiment neither uses a water tank upon measurement of the humidities nor performs a water-refilling operation and the like. Due to the aforementioned reasons, the environmental measurement system according to this embodiment is suitable for measurement of the temperatures and the humidities in many measurement positions in a facility such as a data center, a large office building or a factory.

Figure 10:
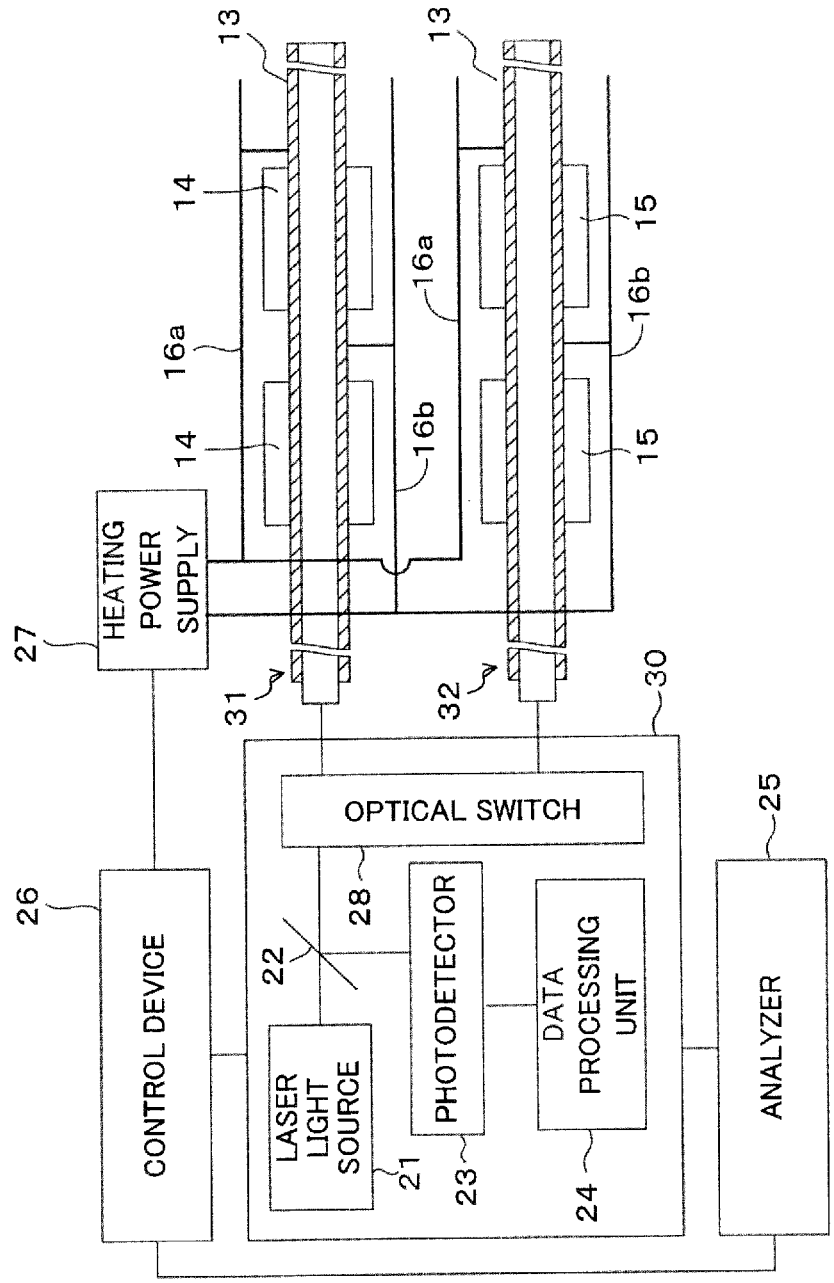
FIG. 10 is a block diagram illustrating a modification of the first embodiment.

In this embodiment, the single optical fiber 10 is provided with the hygroscopic layer 14 and the non-hygroscopic layer 15. Instead, as illustrated in FIG. 10, it may be also possible to use two optical fibers, namely, an optical fiber (a first optical fiber) 31 including the hygroscopic layer 14 but not including the non-hygroscopic layer 15, and an optical fiber (a second optical fiber) 32 including the non-hygroscopic layer 15 but not including the hygroscopic layer 14. In this case, a temperature measurement device 30 provided with an optical switch 28 is used and this optical switch 28 controls optical connection among the laser light source 21, the beam splitter 22, and the optical fibers 31 and 32. For example, a Raman scattered light measurement device (DTS800M: manufactured by SENSA) used as the temperature measurement device in Experiment 1 to be described later optically switches the connection among the plurality of optical fibers, the laser light source, and the beam splitter by means of an optical switch embedded therein. Here, it may be also possible to use a temperature measurement device provided with a plurality of sets of the laser light source 21, the beam splitter 22, and the photodetector 23 instead of the temperature measurement device 30 configured to switch the optical connection by means of the optical switch 28.

Although this embodiment is configured to form the heat generation layer (the heater) integrally with the optical fiber 10, the hygroscopic layer 14 and the non-hygroscopic layer 15 may be heated by use of a heater provided separately from the optical fiber. In addition, this embodiment is configured to measure the temperature distribution by using the Raman scattered light (the Stokes light and the anti-Stokes light). However, it may be also possible to measure the temperature distribution by using the Brillouin scattered light.

Experimental results of actual measurement of the temperatures and the humidities in accordance with the environmental measurement method of this embodiment will be described below.

Experiment 1

A multimode graded-index quartz optical fiber (HFR-2Z-1: manufactured by Furukawa Electric Co., Ltd.) is used for the optical fiber serving as the sensor. This optical fiber is formed by covering the core wire 11 with polyurethane resin. This polyurethane resin layer is defined as the insulating covering layer 12. The diameter of the optical fiber (the outside diameter of the insulating covering layer 12) is set to 250 μm and the diameter of the core wire 11 is set to 125 μm.

Portions of the heat generation layers 13 are formed around this optical fiber by coating polyester-based silver paste (DW-250H-5: manufactured by Toyobo Co., Ltd.) at a length of 2 m each and a pitch of 4 m along the longitudinal direction of the optical fiber in accordance with a dipping method. The heat generation layers 13 have a thickness of 10 μm. The silver paste is coated on the peripheral surface of the optical fiber by the dipping method and is then dried for 30 minutes in an atmosphere at a temperature of 100° C.

Next, each portion of the heat generation layer 13 is divided into two 1-meter regions along the longitudinal direction of the optical fiber, and the hygroscopic layer 14 is formed in a thickness of 0.3 mm on one of the regions by coating a hygroscopic layer material thereon. Here, paste prepared by mixing 10 parts by weight of an ultraviolet-setting silicone varnish (X-31-2011-1: manufactured by Shin-Etsu Chemical Co., Ltd.) and 1 part by weight of calcium chloride powder in a ball mill for 1 hour is used as the hygroscopic layer material.

In the meantime, the non-hygroscopic layer 15 is formed in a thickness of 0.3 mm on the other region of the heat generation layer 13 by coating the same vanish (note that no calcium chloride is contained therein) as the one used for forming the hygroscopic layer 14. Here, both of the hygroscopic layer material and the non-hygroscopic layer material are coated on the heat generation layer 13 and are then set by irradiating the materials with light (ultraviolet rays) from a high-pressure mercury lamp (160 W/cm) while pulling the optical fiber at a rate of 1 m/min.

Next, two electric wires are arranged parallel to the optical fiber and the two electric wires are electrically connected to the heat generation layer 13 by using urethane curing type silver paste (3302B: manufactured by ThreeBond Co., Ltd.). The urethane curing type silver paste is coated in dot shapes between the electric wires and the heat generation layer 13 by using a dispenser and is then dried for 1 hour at a temperature of 120°.

The optical fiber provided with the hygroscopic layer 14 and the non-hygroscopic layer 15 is placed in a constant temperature and humidity tank which may maintain a predetermined temperature and a predetermined humidity. Then, a terminal end of the optical fiber is connected to a Raman scattered light measurement device (DTS800M: manufactured by SENSA) serving as the temperature measurement device 20.

In addition, a capacitance type hygrometer is also installed in the constant temperature and humidity tank. Then, the humidities are measured with use of the capacitance type hygrometer and in accordance with the environmental measurement method of this embodiment while changing the humidities in the constant temperature and humidity tank from 10% RH to 90% RH. According to the environmental measurement method of this embodiment, the Raman scattered light measurement device measures the temperatures at the portions where the hygroscopic layer 14 and the non-hygroscopic layer 15 are installed. Then, the area S surrounded by the curve indicating the temperature rise at the portion where the hygroscopic layer 14 is provided and the curve indicating the temperature rise at the portion where the non-hygroscopic layer 15 is provided is calculated, and the value of the area S is converted into the humidity by using the humidity conversion table which is prepared in advance and configured to indicate the relation between the area S and the relative humidity.

Figure 11:
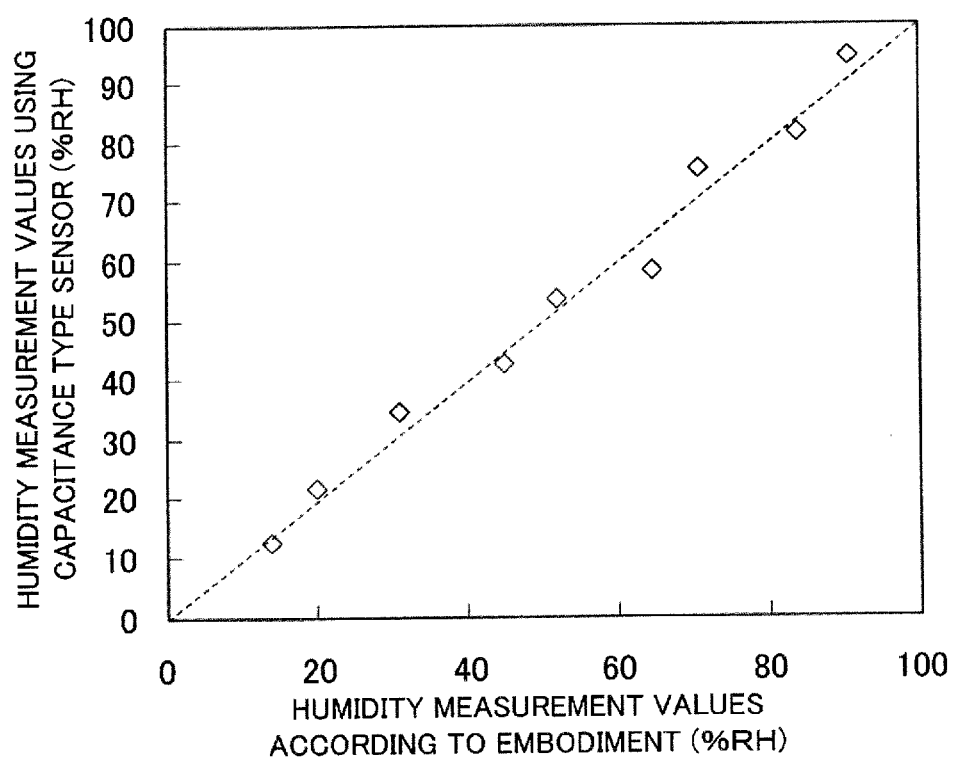
FIG. 11 is a view illustrating a correlation between humidity measurement values according to the environmental measurement method of the embodiment and humidity measurement values using a capacitance type hygrometer.

FIG. 11 is a view illustrating a correlation between humidity measurement values according to the environmental measurement method of this embodiment and humidity measurement values using the capacitance type hygrometer. As illustrated in FIG. 11, it is confirmed that the humidities measured in accordance with the environmental measurement method of this embodiment closely agree with the humidities measured by using the capacitance type hygrometer with errors not exceeding 10%.

In the environmental measurement method of this embodiment, the power consumption in the case of performing the environmental measurement by using the optical fiber having the entire length of 2 km is approximately equal to or below 300 W.

Experiment 2

Two optical fibers (HFR-2Z-1: manufactured by Furukawa Electric Co., Ltd.) which are the same as the one used in Experiment 1 are prepared (see FIG. 10). Then, the heat generation layers 13 are formed on the optical fibers. Thereafter, the hygroscopic layer 14 is formed in a thickness of 0.3 mm on one of the optical fibers (a first optical fiber 31) by coating a hygroscopic layer material, and the non-hygroscopic layer 15 is formed in a thickness of 0.3 mm on the other optical fiber (a second optical fiber 32) by coating a non-hygroscopic layer material. Paste prepared by mixing and dispersing 1 part by weight of magnesium chloride powder into 10 parts by weight of polyvinylidene fluoride (KF-1100: manufactured by Kureha Corporation) is used as the hygroscopic layer material. In the meantime, the same polyvinylidene fluoride (note that no magnesium chloride is contained therein) as the one used for forming the hygroscopic layer 14 is used as the non-hygroscopic layer material.

The first optical fiber 31 and the second optical fiber 32 are arranged in the constant temperature and humidity tank while providing a clearance of 5 mm therebetween. Then, terminal ends of the two optical fibers 31 and 32 are connected to the Raman scattered light measurement device (DTS800M: manufactured by SENSA) serving as the temperature measurement device 30.

In addition, a capacitance type hygrometer is also installed in the constant temperature and humidity tank. Then, the humidities are measured with use of the capacitance type hygrometer and in accordance with the environmental measurement method of this embodiment while changing the humidities in the constant temperature and humidity tank from 10% RH to 90% RH. As a result, the differences between the humidities measured in accordance with the environmental measurement method of this embodiment and the humidities measured by using the capacitance type hygrometer are equal to or below 10%.

Second Embodiment

Figure 12:
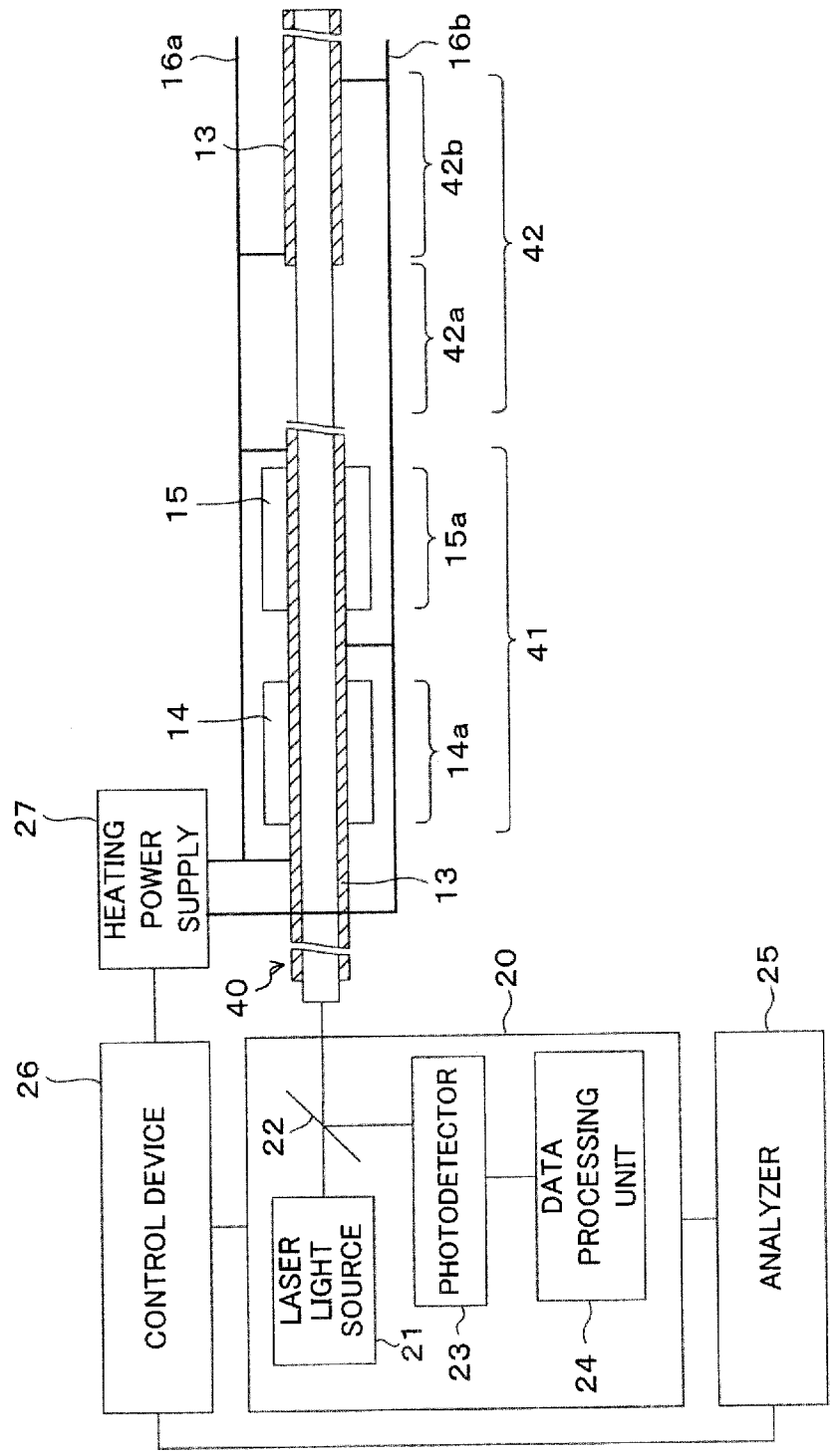
FIG. 12 is a block diagram illustrating an outline of an environmental measurement system according to a second embodiment.

FIG. 12 is a block diagram illustrating an outline of an environmental measurement system according to a second embodiment. In FIG. 12, the constituents which are the same as those in FIG. 1 will be denoted by the same reference numerals and detailed description thereof will be omitted.

An optical fiber 40 used in this embodiment includes a temperature measurement portion 41 and a wind velocity measurement portion 42. The temperature measurement portion 41 includes the wet measurement portion 14a provided with the hygroscopic layer 14 and the dry measurement portion 15a provided with the non-hygroscopic layer 15 as similar to the first embodiment. The humidity in the atmosphere is calculated based on the temperature variations at the dry measurement portion 15a and the wet measurement portion 14a.

Meanwhile, the wind velocity measurement portion 42 includes an atmospheric temperature measurement portion 42a where an insulating covering layer (not illustrated in FIG. 12) is exposed without provision of the heat generation layer 13 and a heated temperature measurement portion 42b where the heat generation layer 13 is provided around the insulating covering layer. When electric power is supplied to the heat generation layer 13 at this heated temperature measurement portion 42b, the heat generation layer 13 is brought into resistance heating and the temperature to be detected with the temperature measurement device 20 is thereby increased. Here, assuming that the atmospheric temperature is constant, a peak temperature becomes lower as the wind velocity in a position where the wind velocity measurement portion 42 is installed is higher. In the meantime, the detected temperature drops over time after the power supply to the heat generation layer 13 is stopped. Here, the time for returning to the room temperature becomes shorter as the wind velocity in the position where the wind velocity measurement portion 42 is installed is higher. In other words, the wind velocity in the position where the wind velocity measurement portion 42 is installed may be detected by use of the peak temperature or the time for returning to the room temperature.

In addition to the humidity conversion table, the analyzer 25 stores a wind velocity conversion table indicating relations among the atmospheric temperature, the peak temperature, and the wind velocity. Then, the analyzer 25 calculates the humidity based on the temperature variations at the humidity measurement portion 41 (the wet measurement portion 14a and the dry measurement portion 15a) outputted from the temperature measurement device 20. Moreover, the analyzer 25 calculates the wind velocity based on the atmospheric temperature detected by the wind velocity measurement portion 42 (the atmospheric temperature measurement portion 42a and the heated temperature measurement portion 42b) and on the temperature variation detected by the heated temperature measurement portion 42b. Here, it is important to install the wind velocity measurement portion 42 on the way of passage of the wind while it is important to install the humidity measurement portion 41 in a place not directly exposed to the wind.

According to this embodiment, the temperatures, the humidities, and the wind velocities in a plurality of positions may be measured by using the single optical fiber 40. Accordingly, this embodiment involves a simpler system configuration as compared to a system constructed by individually installing a temperature sensor, a humidity sensor, and a wind velocity sensor in each of measurement positions, thereby reducing costs for constructing the system and costs for maintenance.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present inventions have been described in detail, it should be understood that the various changes, substitutions, and alterations could be made hereto without departing from the spirit and scope of the invention.

What is claimed is:

1. An environmental measurement system comprising:
an optical fiber including a first measurement portion covered with a hygroscopic layer having a moisture absorption capacity to absorb moisture in an atmosphere, and a second measurement portion covered with a non-hygroscopic layer having a lower moisture absorption capacity than the capacity of the hygroscopic layer;
a heater configured to heat the first measurement portion and the second measurement portion;
a temperature measurement device configured to input light into the optical fiber, and to receive backscattered light outputted from the optical fiber to measure temperature distribution in a longitudinal direction of the optical fiber;
an analyzer configured to analyze a variation over time of the temperature distribution outputted from the temperature measurement device to calculate a temperature and a humidity in a measurement position where the first measurement portion and the second measurement portion are installed; and
a control device configured to control the heater, the temperature measurement device, and the analyzer.

2. The environmental measurement system according to claim 1, wherein the optical fiber comprises a plurality of the first measurement portions and a plurality of the second measurement portions arranged along the longitudinal direction of the optical fiber.

3. The environmental measurement system according to claim 1, wherein the analyzer calculates the humidity in the measurement position based on an integrated value of differences between the temperatures at the first measurement portion and the temperatures at the second measurement portion when the measurement portions are heated by the heater.

4. The environmental measurement system according to claim 1, wherein the hygroscopic layer is made of a material in which a substance having a deliquescent property is dispersed into a resin of a parent material.

5. The environmental measurement system according to claim 4, wherein the non-hygroscopic layer is made of the same resin as the resin of the parent material of the hygroscopic layer.

6. The environmental measurement system according to claim 4, wherein the substance having the deliquescent property is any of magnesium chloride, calcium chloride, sodium acetate, and diphosphorus pentoxide.

7. The environmental measurement system according to claim 4, wherein the resin of the parent material is any of polyvinylidene fluoride, polyvinylidene chloride, and silicone resin.

8. The environmental measurement system according to claim 1, wherein the hygroscopic layer is made of resin having any of a deliquescent property and a hygroscopic property.

9. The environmental measurement system according to claim 8, wherein the resin is any of polystyrene sulfonate and quaternized polyvinylpyridine.

10. The environmental measurement system according to claim 1, wherein the optical fiber further includes a wind velocity measurement portion configured to measure a wind velocity.

11. An environmental measurement system comprising:
a first optical fiber including a first measurement portion covered with a hygroscopic layer having a moisture absorption capacity to absorb moisture in an atmosphere:
a second optical fiber including a second measurement portion covered with a non-hygroscopic layer having a lower moisture absorption capacity than the capacity of the hygroscopic layer;
a first heater configured to heat the first measurement portion of the first optical fiber;
a second heater configured to heat the second measurement portion of the second optical fiber;
a temperature measurement device configured to input light into the first optical fiber and the second optical fiber, and to receive backscattered light outputted from the first optical fiber and the second optical fiber to measure temperature distribution in a longitudinal direction of each of the first optical fiber and the second optical fiber;
an analyzer configured to analyze a variation over time of the temperature distribution outputted from the temperature measurement device to calculate a temperature and a humidity in a measurement position where the first measurement portion and the second measurement portion are installed; and
a control device configured to control the first heater, the second heater, the temperature measurement device, and the analyzer.

12. An environmental measurement method comprising:
installing a first measurement portion and a second measurement portion of an optical fiber in a given measurement position;
heating the first measurement portion and the second measurement portion while inputting light into the optical fiber and measuring a variation over time of temperatures at the first measurement portion and a variation over time of temperatures at the second measurement portion by using backscattered light outputted from the optical fiber; and
calculating a temperature and a humidity in the measurement position based on the temperature variation at the first measurement portion and the temperature variation at the second measurement portion, wherein
the first measurement portion and the second measurement portion of the optical fiber respectively include covering layers having mutually different moisture absorption capacities to absorb moisture in an atmosphere.

13. The environmental measurement method according to claim 12, wherein an integrated value of differences between the temperatures at the first measurement portion and the temperatures at the second measurement portions is calculated in the calculating a temperature, and the integrated value is converted into a humidity by using a relation between an integrated value and a humidity prepared in advance.

* * * * *